(12) United States Patent
Salvi et al.

(10) Patent No.: US 6,844,450 B2
(45) Date of Patent: Jan. 18, 2005

(54) PROCESS FOR THE PRODUCTION OF A RACEMIC THIOCTIC ACID

(75) Inventors: Annibale Salvi, Milan (IT); Stefano Maiorana, Milan (IT); Francesco Corcella, Parabiago (IT)

(73) Assignee: Laboratorio Chimico Internazionale S.p.A., Milan (IT)

(*) Notice: Subject to any disclaimer, the term of this patent is extended or adjusted under 35 U.S.C. 154(b) by 0 days.

(21) Appl. No.: 10/398,891

(22) PCT Filed: Oct. 8, 2001

(86) PCT No.: PCT/EP01/11577

§ 371 (c)(1),
(2), (4) Date: Apr. 9, 2003

(87) PCT Pub. No.: WO02/30917

PCT Pub. Date: Apr. 18, 2002

(65) Prior Publication Data

US 2004/0030157 A1 Feb. 12, 2004

(30) Foreign Application Priority Data

Oct. 10, 2000 (IT) .................................. MI2000A2186

(51) Int. Cl.$^7$ ............................................. C07D 341/00
(52) U.S. Cl. ........................................... 549/39; 554/25
(58) Field of Search .............................. 549/39; 554/125

(56) References Cited

U.S. PATENT DOCUMENTS 2,792,406 A   5/1957  Acker
5,731,448 A * 3/1998  Gewald et al. ............... 554/85
6,140,512 A  10/2000  Adger et al.

OTHER PUBLICATIONS

The Merck Index, 1984, p. 870.*
G. Bringmann et al., "A Short And Productive Synthesis Of (R)–Alfpha–Lipoic Acid," Zeitschrift Fur Naturforschung, Tell B: Anorganische Chemie, Organische Chemie, Verlag Der Zeitschrift Fur Naturforschung, Tubingen pp. 655–661 (1999).

* cited by examiner

Primary Examiner—Rita Desai
Assistant Examiner—Robert Shiao
(74) Attorney, Agent, or Firm—Nixon Peabody LLP

(57) ABSTRACT

Process for the synthesis of racemic thioctic acid comprising the following stages: a) reaction of the alkyl ester of 6,8-di-halo-octanoic acid in an organic solvent with an aqueous solution of alkali disulfide in presence of a compound for phase transfer catalysis selected from the group consisting of quaternary ammonium or phosphonium salts having the following general formula: where: A is nitrogen of phosphorus, X is selected from the group consisting of Cl, Br, I, $HSO_4$, and $H_2PO_4$ and the substitutents $R_1$, $R_2$, $R_3$ and $R_4$ are selection from the group consisting of linear or branched alkyl radicals having one to twenty carbon atoms (C1–C20), said substituents being identical or different one from the other, or only one of said substituents is selected from the group consisting of arylalkyl radicals having the following formula —$(CH_2)_n C_6 H_5$ in which n=1–16; b) followed by the hydrolysis of the ester of racemic thiotic acid.

(I)

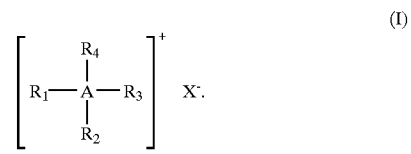

20 Claims, No Drawings

PROCESS FOR THE PRODUCTION OF A RACEMIC THIOCTIC ACID

FIELD OF THE INVENTION

The present invention relates to a process of synthesis of racemic thioctic acid with phase transfer catalysis.

STATE OF THE ART

The state of the art describes processes of synthesis of racemic thioctic acid by reaction between sodium disulfide ($Na_2S_2$), which is obtained in its turn from sulfur (S) and sodium sulfide ($Na_2S$), and an alkyl ester of 6,8-dichlorooctanoic acid. Said processes are characterized by low yields (see J.A.C.S. Volume 79, 1957, page 6486). There was therefore the need to provide a process for the synthesis of racemic thioctic acid with high yield starting from the alkyl esters of 6,8-dichlorooctanoic acid.

SUMMARY

It has now been found a new process of synthesis of racemic thioctic acid starting from the alkyl esters of 6,8-di-halo-octanoic acid, which can overcome the disadvantages characterizing the processes at the state of the art such as low yields and low quality. Quite unexpectedly and surprisingly, the Applicant has found a new process for the synthesis of racemic thioctic acid starting from the alkyl esters of 6,8-di-halo-octanoic acid, based on phase transfer catalysis, which allows to obtain a pure product with high yield.

DETAILED DESCRIPTION OF THE INVENTION

An object of the present invention is therefore a process of synthesis of racemic thioctic acid comprising the following stages:

a) reaction of the alkyl ester of 6,8-di-halo-octanoic acid in an organic solvent with an aqueous solution of alkali disulfide in presence of a compound for phase transfer catalysis selected from the group consisting of quaternary ammonium or phosphonium salts having the following general formula:

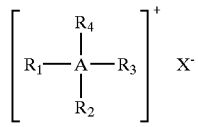

where:

A is nitrogen of phosphorus,

X is selected from the group consisting of Cl, Br, I, $HSO_4$ and $H_2PO_4$, and the substituents $R_1$, $R_2$, $R_3$ and $R_4$ are selected from the group consisting of linear or branched alkyl radicals having one to twenty carbon atoms ($C_1$–$C_{20}$), said substituents being identical or different one from the other, or only one of said substituents is chosen from the group comprising arylalkyl radicals having the following formula —$(CH_2)_nC_6H_5$ in which n=1–16;

b) followed by the hydrolysis of the ester of racemic thioctic acid.

According to the present invention the alkyl esters of 6,8-di-halo-octanoic acid are linear or branched $C_1$–$C_6$ esters, and the halogen substituents, identical or different one from the other, are chosen from the group consisting of Cl, Br or I.

The alkyl esters of 6,8-di-halo-octanoic acid are preferably linear or branched $C_1$–$C_3$ esters, and the halogen substituents, identical or different one from the other, are Cl or Br.

Still more preferably, the alkyl esters of 6,8-di-halo-octanoic acid are methyl ester or ethyl ester of 6,8-dichlorooctanoic acid.

According to the present invention, the amount of alkyl esters of 6,8-di-halo-octanoic acid in the reaction taking place in stage a) is between 5 and 60% by weight, preferably between 10 and 40% by weight, still more preferably between 15 and 30% by weight with respect to the organic solvent.

The organic solvent used in the reaction taking place in stage a) is a solvent which cannot be mixed with water, selected from the group consisting of: linear or branched aliphatic $C_5$–$C_{10}$ hydrocarbons, or aromatic $C_5$–$C_{10}$ hydrocarbons also having substituting groups selected from the group consisting of halogen, nitro or nitrile groups; esters of aliphatic or aromatic carboxylic acids; linear or cyclic ethers; linear or cyclic $C_4$–$C_{10}$ ketones, carbon disulfide, carbon tetrachloride. The solvent is preferably benzene or toluene.

The process of synthesis of racemic thioctic acid according to present invention comprises the phase transfer of the disulfide ion from the aqueous solution containing the corresponding alkali disulfide to the organic phase which cannot be mixed with water, containing the alkyl ester of 6,8-di-halo-octanoic acid. The aqueous solution of alkali disulfide can be prepared by reacting in water sulfur (S) with the corresponding alkali sulfide.

Preferred alkali disulfides are sodium disulfide ($Na_2S_2$) and potassium disulfide ($K_2S_2$) or their mixtures, still more preferred sodium disulfide.

In the reaction taking place in stage a) of the process of synthesis of racemic thioctic acid according to the present invention, the molar ratio alkali disulfide/alkyl ester of 6,8-di-halo-octanoic acid is between 0.8 and 1.2, preferably between 0.9 and 1.1, still more preferably between 0.95 and 1.0.

The compounds for phase transfer catalysis used for the synthesis of thioctic acid which is the object of the present invention, are selected from the group consisting of tetrabutylammonium bromide, tetrabutylphosphonium bromide, methyltrioctylammonium chloride (ALIQUAT® 336), methyl-($C_8$–$C_{10}$)-trialkylammonium chloride (ADOGEN® 464) and tetrabutylammonium hydrogensulfate; still more preferred are tetrabutylammonium bromide and tetrabutylammonium hydrogensulfate.

According to the process of synthesis described in the present invention, in the reaction taking place in stage a) the compound for phase transfer catalysis, a quaternary salt, is present in an amount between 0.5 to 10% in moles, preferably between 1 to 5% in moles, still more preferably between 2 to 4% in moles with respect to the alkyl ester of 6,8-di-halo-octanoic acid.

The temperature of the reaction taking place in stage a) is between 20 and 130° C., preferably between 60 and 100° C., still more preferably between 80 and 90° C.

Stage b), i.e. hydrolysis of the ester of racemic thioctic acid is a hydrolysis with alkali/alkaline-earth hydroxides in presence of organic solvents, such as alcohols and polyols, ethers and hydroxy ethers, ketones and hydroxy ketones, which can be mixed with water in a volume ratio of 50:50 to 95:5 at a temperature between 0 and 100° C. The concentration of the ester with respect to the organic solvent is between 5 and 50% w/v and the molar ratio ester/hydroxide is between 0.5 and 1. Free racemic thioctic acid can be recovered by treatment with aqueous mineral acids diluted 1 to 20% by weight or water-soluble organic acids.

Reaction products and intermediate products are characterized with $^1$H-NMR, Mass, HPLC analyses and potentiometric titration.

The following area some examples disclosing though not limiting the present invention.

EXAMPLE 1

Synthesis of Ethyl Ester of Racemic Thioctic Acid

A mixture consisting of 16.91 g (0.13 moles) of sodium sulfide 60% by weight, 3.57 g (1.1 moles) of sulfur and 65 ml of water is heated at 85° C. for 30 minutes. After being filtered to remove the insoluble portion, the solution is added in three hours to a solution consisting of 29.8 g (0.123 moles) of ethyl 6,8-dichlorooctanoate, 1.4 g (0.003 moles) of tetrabutylammonium bromide and 66 ml of toluene, kept at 82° C. The mixture is refluxed (90° C.) for 1 hour and cooled down at 30° C., the organic phase is separated and washed with 13 ml of water. The whole is concentrated under vacuum, thus obtaining 25.8 g of ethyl ester of thioctic acid (yield=90%).

The final product is characterized by means of $^1$H-NMR and Mass analyses:

$^1$H-NMR-δ (300 MHz, CDCl$_3$): 1.2 (3H, t); 1.4 (2H, m); 1.65 (4H, m); 1.85 (1H, td); 2.25 (2H, t); 2.4 (1H, td); 3.1 (2H, m); 3.5 (1H, m); 4.1 (2H, q).

Mass (EI): 234 (M$^+$); 189 (—CH$_3$CH$_2$O).

EXAMPLE 2

Hydrolysis of Ester of Thioctic Acid 25.8 g (0.11 moles) of ethyl ester of thioctic acid are added to a solution consisting of 9.88 g (0.152 moles) of potassium hydroxide at 90% by weight, 74 ml of methanol and 13.5 ml of water. The mixture obtained is heated at 50° C. for 2 hours and cooled down at 30° C., then 220 ml of toluene are added. The whole is acidified with phosphoric acid 10% by weight, keeping temperature between 30 and 40° C. The organic phase is separated and washed three times, each time with 50 ml of an aqueous solution of sodium chloride at 10% by weight. The organic phase is concentrated by solvent evaporation under vacuum and the residue obtained is cooled down at 0–5° C. for 8–10 hours. The wax-like solid is filtered, thus obtaining 18.2 g of raw thioctic acid (yield=80.3%). Said raw product is purified by dispersion under stirring in 6 ml of toluene and following crystallization from cyclohexane/ethyl acetate. 14.6 g of thioctic acid are obtained. The total yield is of 64%.

The thioctic acid obtained is thus characterized:
melting point: 60–62° C.
titer >99% (HPLC, potentiometric titration)
HPLC purity >99%

What is claimed is:
1. A process for the synthesis of racemic thioctic acid comprising the following stages:
a) reaction of the alkyl ester of 6,8-di-halo-octanoic acid in an organic solvent with an aqueous solution of alkali disulfide in presence of a compound for phase transfer catalysis selected from the group consisting of quaternary ammonium or phosphonium salts having the following general formula:

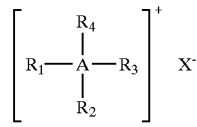

where:
A is nitrogen of phosphorus,
X is selected from the group consisting of Cl, Br, I, HSO$_4$ and H$_2$PO$_4$ and the substituents R$_1$, R$_2$, R$_3$ and R$_4$ are selected from the group consisting linear or branched alkyl radicals having one to twenty carbon atoms (C$_1$–C$_{20}$), said substituents being identical or different one from the other;
followed by the hydrolysis of the ester of racemic thioctic acid;
wherein in the reaction taking place in stage a) the molar ratio alkali disulfide/alkyl ester of 6,8-di-halo-octanoic acid is between 0.8 and 1.2, and said quaternary ammonium or phosphonium salt is present in an amount of 0.5 to 10% in moles with respect to the alkyl ester of 6,8-di-halo-octanoic acid.

2. The process according to claim 1, wherein the alkyl esters of 6,8-di-halo-octanoic acid are linear or branched C$_1$–C$_6$ esters, and the halogen substituents, identical or different one from the other, are selected from the group consisting of Cl, Br or I.

3. The process according to claim 2, wherein said alkyl esters of 6,8-di-halo-octanoic acid are linear or branched C$_1$–C$_3$ esters, and the halogen substituents, identical or different one from the other, are Cl or Br.

4. The process according to claim 3, wherein said alkyl esters of 6,8-di-halo-octanoic acid are methyl ester or ethyl ester of 6,8-dichlorooctanoic acid.

5. The process according to claim 1, wherein the amount of alkyl esters of 6,8-di-halo-octanoic acid in the reaction taking place in stage a) is between 5 and 60% by weight with respect to the organic solvent.

6. The process according to claim 5, wherein the amount of said esters is between 10 and 40% by weight with respect to the organic solvent.

7. The process according to claim 6, wherein the amount of said esters is between 15 and 30% by weight with respect to the organic solvent.

8. The process according to claim 1, wherein the organic solvent used in the reaction taking place in stage a) is selected from the group consisting of: linear or branched aliphatic C$_5$–C$_{10}$ hydrocarbons, or aromatic C$_5$–C$_{10}$ hydrocarbons also having substituting groups selected from the group consisting of halogen, nitro or nitrile groups; esters of aliphatic or aromatic carboxylic acids; linear or cyclic ethers; linear or cyclic C$_4$–C$_{10}$ ketones; carbon tetrachloride.

9. The process according to claim 8, wherein said solvent is benzene or toluene.

10. The process according to claim 1, wherein the alkali disulfides are sodium disulfide (Na$_2$S$_2$) or potassium disulfide (K$_2$S$_2$) or their mixture.

11. The process according to claim 10, wherein said alkali disulfide is sodium disulfide.

12. The process according to claim 1, wherein the molar ratio alkali disulfide/alkyl ester of 6,8-di-halo-octanoic acid is between 0.9 and 1.1.

13. The process according to claim 12, wherein said molar ratio is between 0.95 and 1.0.

14. The process according to claim 1, wherein the quaternary ammonium or phosphonium salts are selected from the group consisting of tetrabutylammonium bromide, tetrabutylphosphonium bromide, methyltrioctylammonium chloride, methyl-($C_8$–$C_{10}$)-trialkylammonium chloride and tetrabutylammonium hydrogensulfate.

15. The process according to claim 14, wherein said quaternary salts are tetrabutylammonium bromide or tetrabutylammonium hydrogensulfate.

16. The process according to claim 1, wherein said quaternary salt is present in an amount of 1 to 5% in moles with respect to the alkyl ester of 6,8-di-halo-octanoic acid.

17. The process according to claim 16, wherein said quaternary salt is present in an amount of 2 to 4% in moles with respect to the alkyl ester of 6,8-di-halo-octanoic acid.

18. The process according to claim 1, wherein the temperature of the reaction taking place in stage a) is between 20 and 130° C.

19. The process according to claim 18, wherein said temperature is between 60 and 100° C.

20. The process according to claim 19, wherein said temperature is between 80 and 90° C.

* * * * *